(12) United States Patent
Dobbs

(10) Patent No.: US 7,238,173 B1
(45) Date of Patent: Jul. 3, 2007

(54) TAMPON DISPOSAL SYSTEM

(76) Inventor: Lisa C. Dobbs, 810 N. 4th St., Bismarck, ND (US) 58501

( * ) Notice: Subject to any disclaimer, the term of this patent is extended or adjusted under 35 U.S.C. 154(b) by 0 days.

(21) Appl. No.: 11/264,448

(22) Filed: Nov. 1, 2005

Related U.S. Application Data

(60) Provisional application No. 60/624,648, filed on Nov. 2, 2004.

(51) Int. Cl.
*A61F 13/15* (2006.01)
*A61F 13/20* (2006.01)
*A61B 17/06* (2006.01)
*B65D 69/00* (2006.01)

(52) U.S. Cl. ............ 604/385.13; 604/904; 604/385.17; 604/385.18; 604/385.02; 604/385.11; 604/385.19; 206/438; 206/581

(58) Field of Classification Search ........... 604/385.06, 604/385.13, 385.01, 385.02, 385.17, 904, 604/11–14, 385.18; 206/581, 438, 440, 823, 206/812

See application file for complete search history.

(56) References Cited

U.S. PATENT DOCUMENTS

| | | | |
|---|---|---|---|
| 2,620,684 A | 12/1952 | Guinet | 74/732 |
| 3,674,029 A | 7/1972 | Bates et al. | 128/285 |
| 3,814,099 A | 6/1974 | Kobler | 128/285 |
| 5,193,684 A | 3/1993 | McDonald | 206/581 |
| 5,740,554 A | 4/1998 | Reed | 2/158 |
| 5,988,386 A | 11/1999 | Morrow | 206/581 |
| 6,299,607 B1 | 10/2001 | Osborn, III et al. | 604/385.02 |
| 6,350,931 B1 | 2/2002 | Martin | 604/358 |
| 6,610,037 B2 | 8/2003 | Rosengrant | 604/385.02 |
| 6,687,911 B2 | 2/2004 | Fitz | 2/21 |
| 6,702,116 B2 * | 3/2004 | Hummel | 206/438 |
| 6,911,022 B2 * | 6/2005 | Steger et al. | 604/385.05 |
| 6,994,696 B2 * | 2/2006 | Suga | 604/385.02 |
| 2002/0111597 A1 | 8/2002 | Rosengrant | 604/385.13 |
| 2003/0073970 A1 | 4/2003 | Suga | 604/385.02 |
| 2004/0078866 A1 | 4/2004 | Fitz | 2/163 |
| 2006/0004338 A1 * | 1/2006 | Torkildsen et al. | 604/35.02 |

* cited by examiner

*Primary Examiner*—Jacqueline F. Stephens

(57) ABSTRACT

A tampon disposal system for efficiently and sanitarily removing and disposing of a soiled tampon. The tampon disposal system includes a housing having at least one wall, an inner cavity, a plurality of perforated edges and a cleansing wipe that is enclosed within the housing. Removal of the perforated edges from the housing creates an opening along each perforation thereby exposing the inner cavity of the housing and the cleansing wipe positioned therein. Upon removal of the cleansing wipe, the string attached to a soiled tampon is insertable through the openings of the housing whereby removal and disposal of the tampon can be achieved in a relatively sanitary and efficient manner.

10 Claims, 8 Drawing Sheets

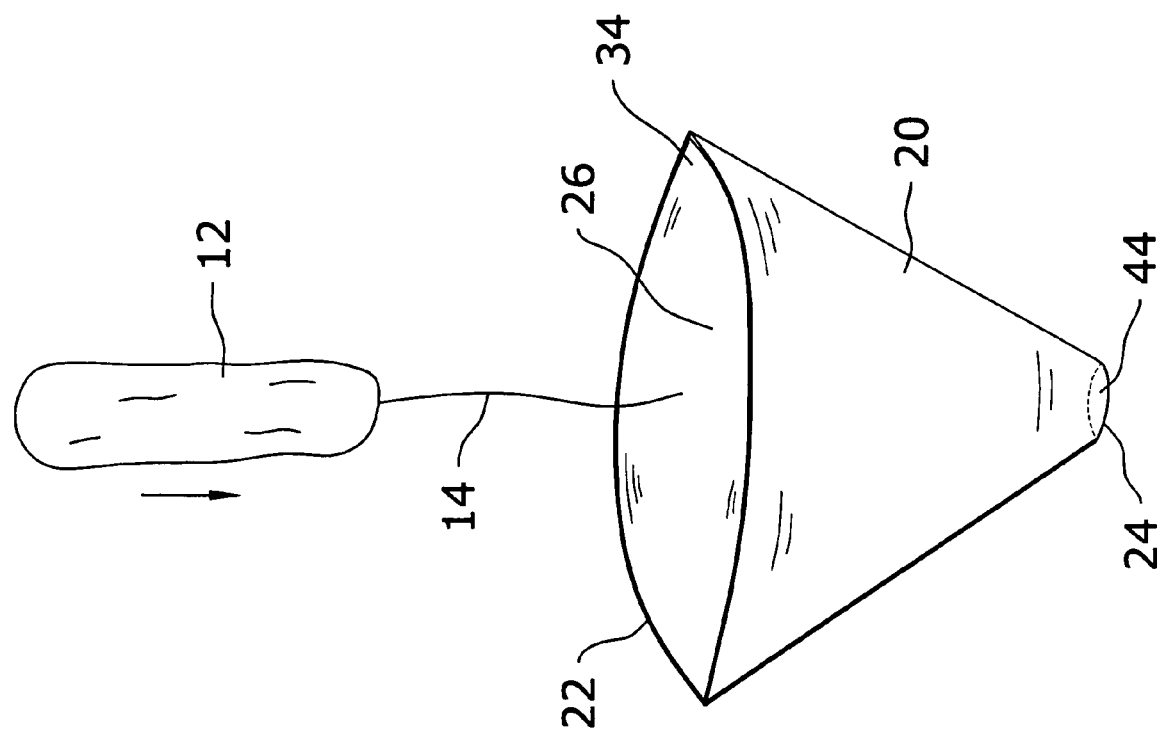

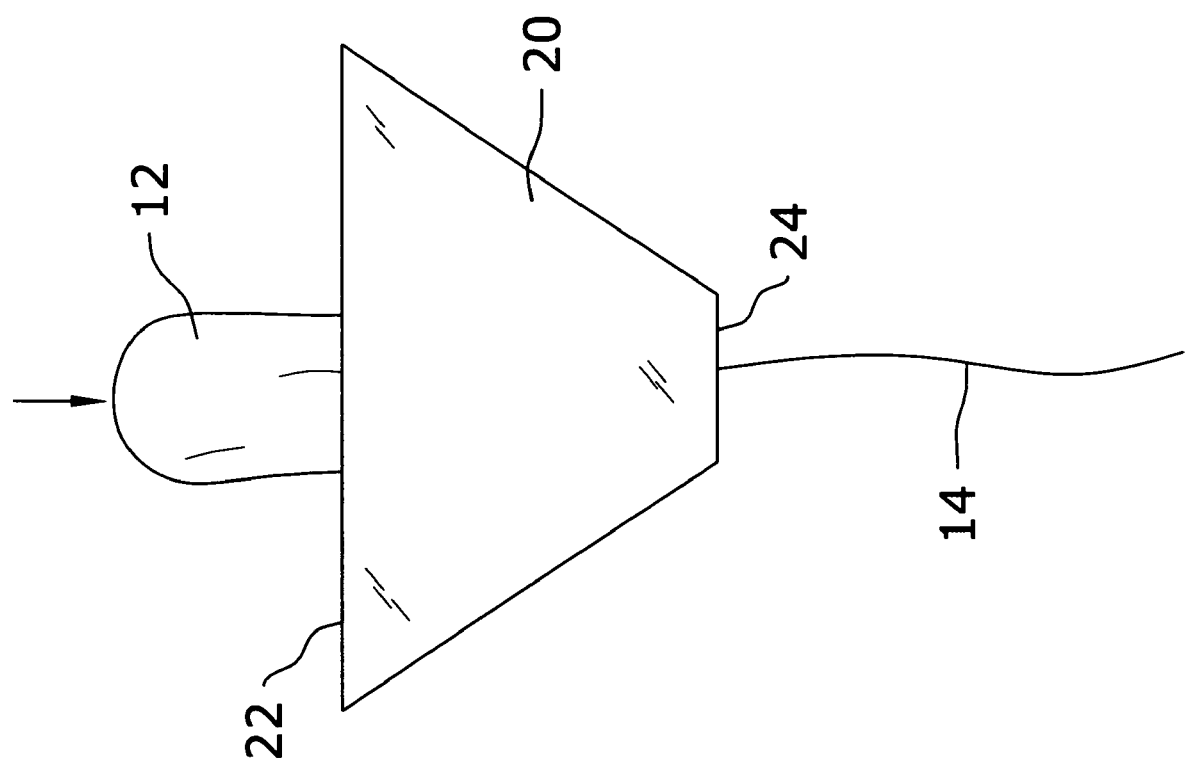

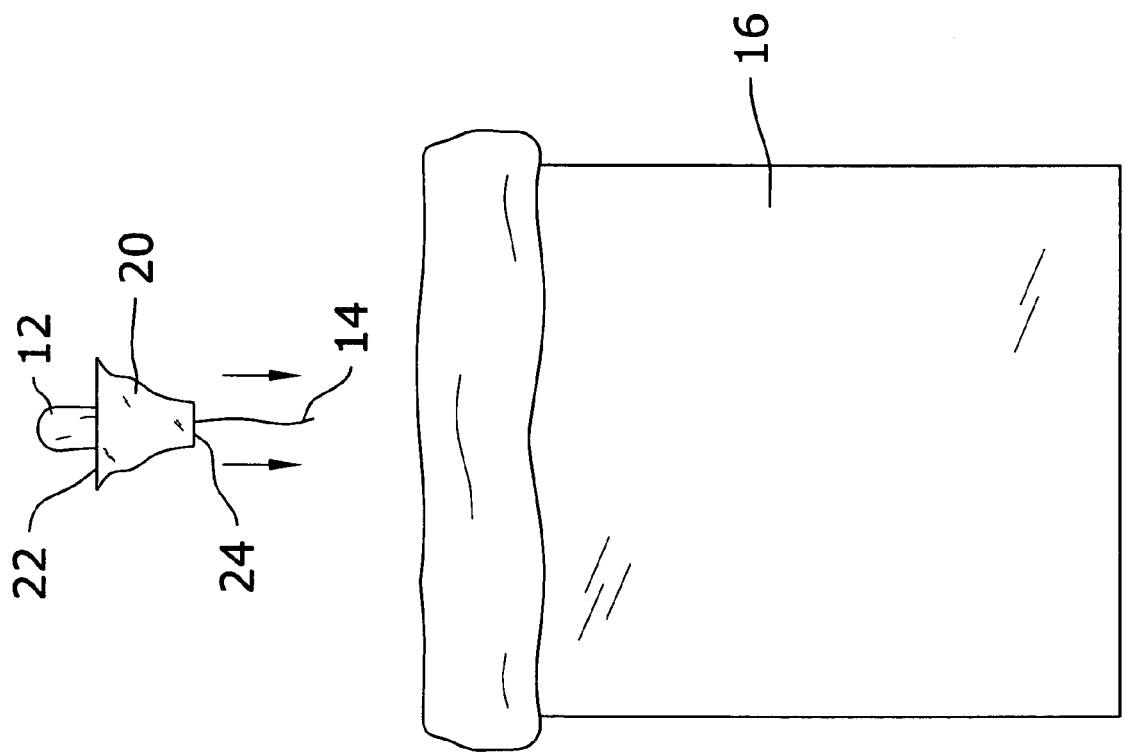

TAMPON DISPOSAL SYSTEM

CROSS REFERENCE TO RELATED APPLICATIONS

I hereby claim benefit under Title 35, United States Code, Section 119(e) of U.S. provisional patent application Ser. No. 60/624,648 filed Nov. 2, 2004. The 60/624,648 application is currently pending. The 60/624,648 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to tampon disposal devices and more specifically it relates to a tampon disposal system for efficiently and sanitarily removing and disposing of a soiled tampon.

2. Description of the Related Art

Any discussion of the prior art throughout the specification should in no way be considered as an admission that such prior art is widely known or forms part of common general knowledge in the field.

Tampon disposal devices have been in use for years. Typically, removal of a soiled tampon requires a user to grasp the string of the tampon to remove it. This is an unsanitary procedure leading to the possibility of bacterial contaminations subsequent to tampon removal.

Another problem associated with tampon removal and disposal concerns the manner in which soiled tampons are disposed. Billions of tampons are discarded each year. Discarding tampons into a toilet causes the tampons to expand. Expansion of these tampons in sewer lines can cause clogged sewer lines and backed up sewer systems.

BRIEF SUMMARY OF THE INVENTION

In view of the foregoing disadvantages inherent in the known types of tampon disposal devices now present in the prior art, the present invention provides a new tampon disposal system construction wherein the same can be utilized for efficiently and sanitarily removing and disposing of a soiled tampon.

The general purpose of the present invention, which will be described subsequently in greater detail, is to provide a new tampon disposal system that has many of the advantages of the tampon disposal devices mentioned heretofore and many novel features that result in a new tampon disposal system which is not anticipated, rendered obvious, suggested, or even implied by any of the prior art tampon disposal devices, either alone or in any combination thereof.

To attain this, the present invention generally comprises a housing having at least one wall, an inner cavity, a plurality of perforated edges and a cleansing wipe that is enclosed within the housing. Removal of the perforated edges from the housing creates an opening along each perforation thereby exposing the inner cavity of the housing and the cleansing wipe positioned therein. Upon removal of the cleansing wipe, the string attached to a soiled tampon is insertable through the openings of the housing whereby removal and disposal of the tampon can be achieved in a relatively sanitary and efficient manner.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a tampon disposal system that will overcome the shortcomings of the prior art devices.

A second object is to provide a tampon disposal system for efficiently and sanitarily removing and disposing of a soiled tampon.

Another object is to provide a tampon disposal system that provides a "hands-free" way of removing a soiled tampon.

An additional object is to provide a tampon disposal system that is easily stored in a purse or pocket.

A further object is to provide a tampon disposal system that promotes discarding a soiled tampon into a refuse container rather than municipal sewage systems.

Another object is to provide a tampon disposal system that provides a cleansing wipe enclosed within a housing for simple and efficient cleansing following removal of a soiled tampon.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 6 is an exploded upper perspective view of the present invention with respect to the tampon.

FIG. 7 is a front view of the present invention having a tampon contained therein.

FIG. 8 is a front view of the present invention illustrating the preferable method of discarding of the tampon and housing into a trash can.

DETAILED DESCRIPTION OF THE INVENTION

A. Overview

Figure 1:
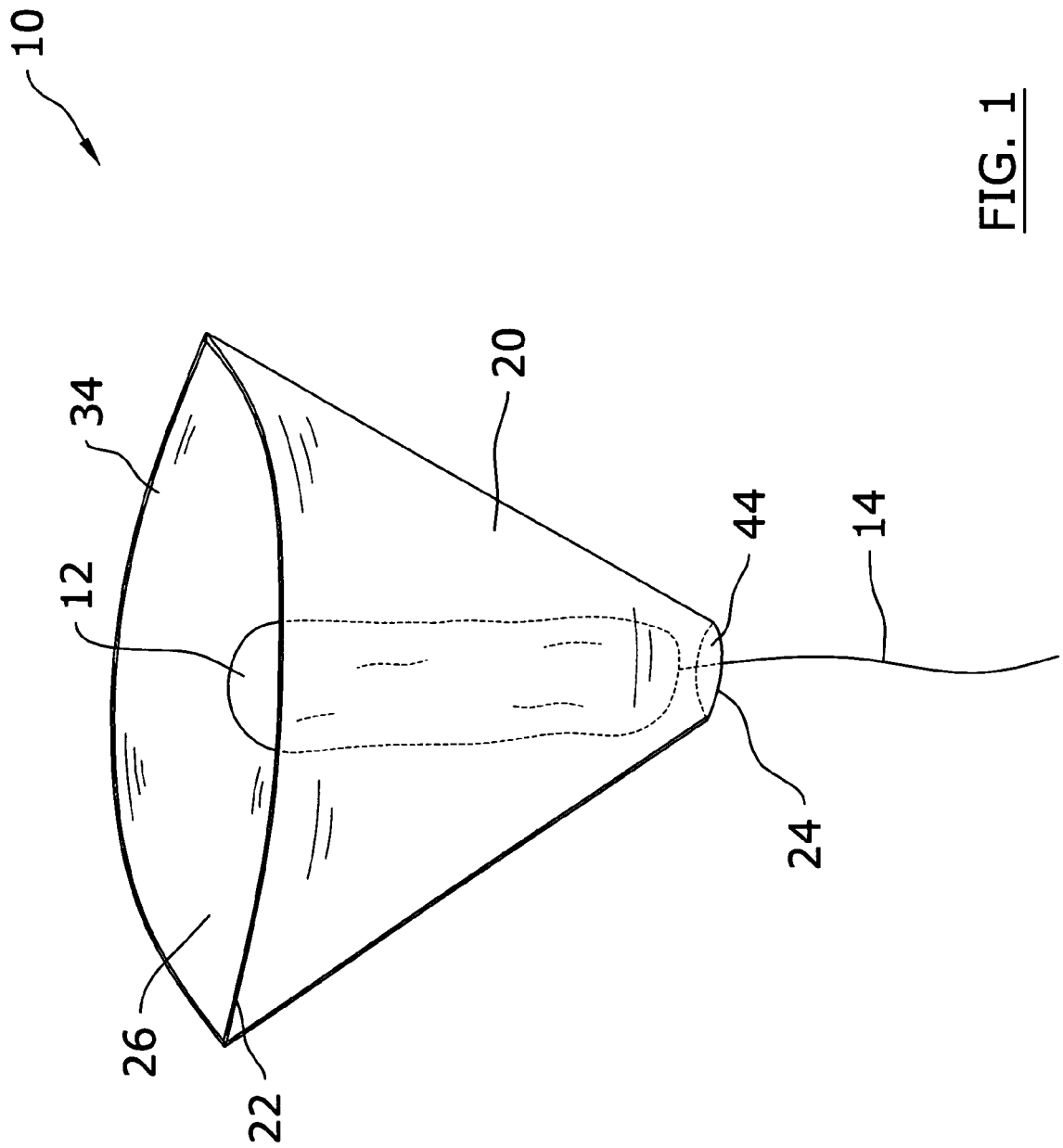
FIG. 1 is an upper perspective view of the present invention having a tampon retained within the housing.
Figure 3:
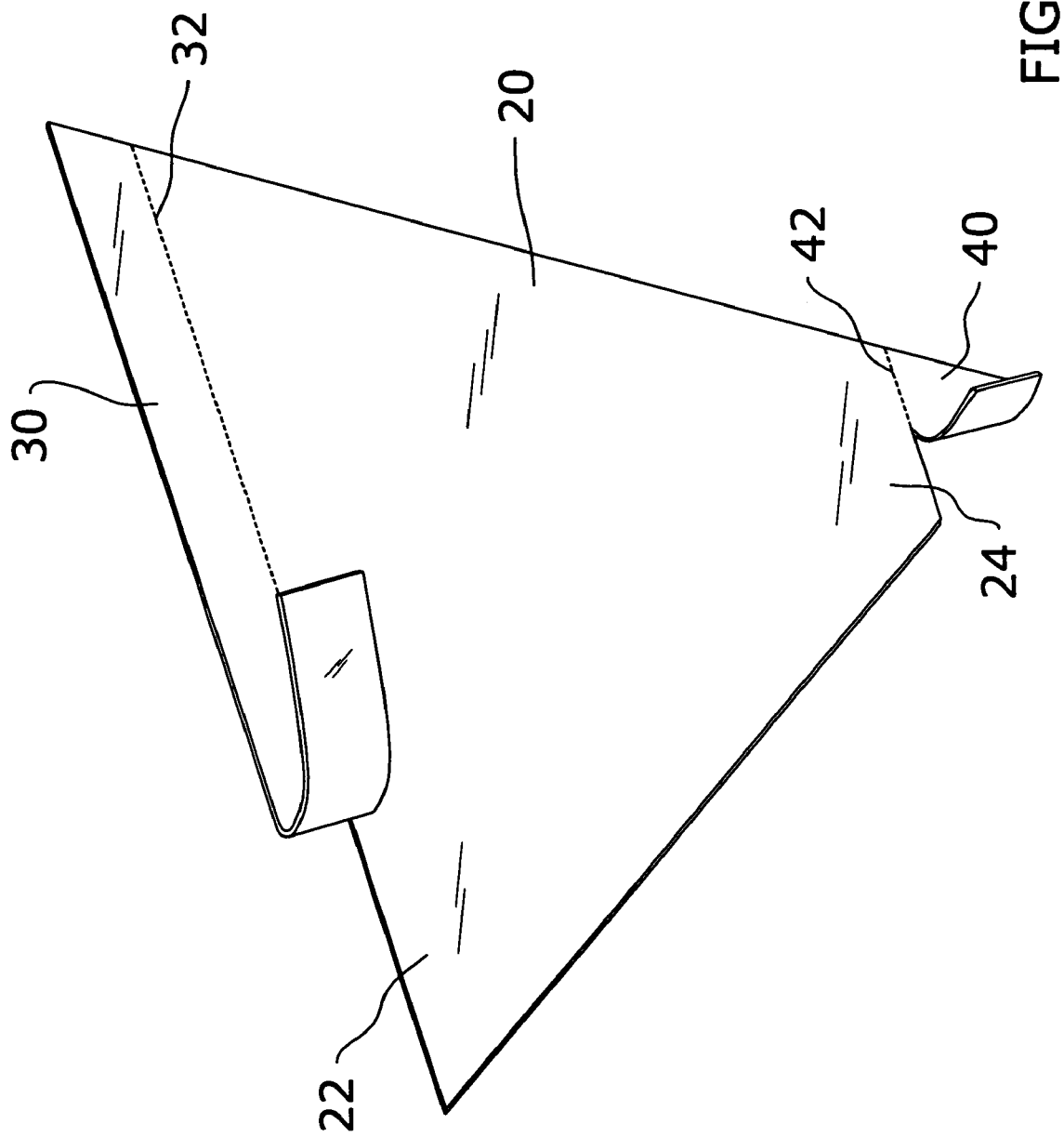
FIG. 3 is an upper perspective view of the present invention illustrating removal of the edges.
Figure 4:
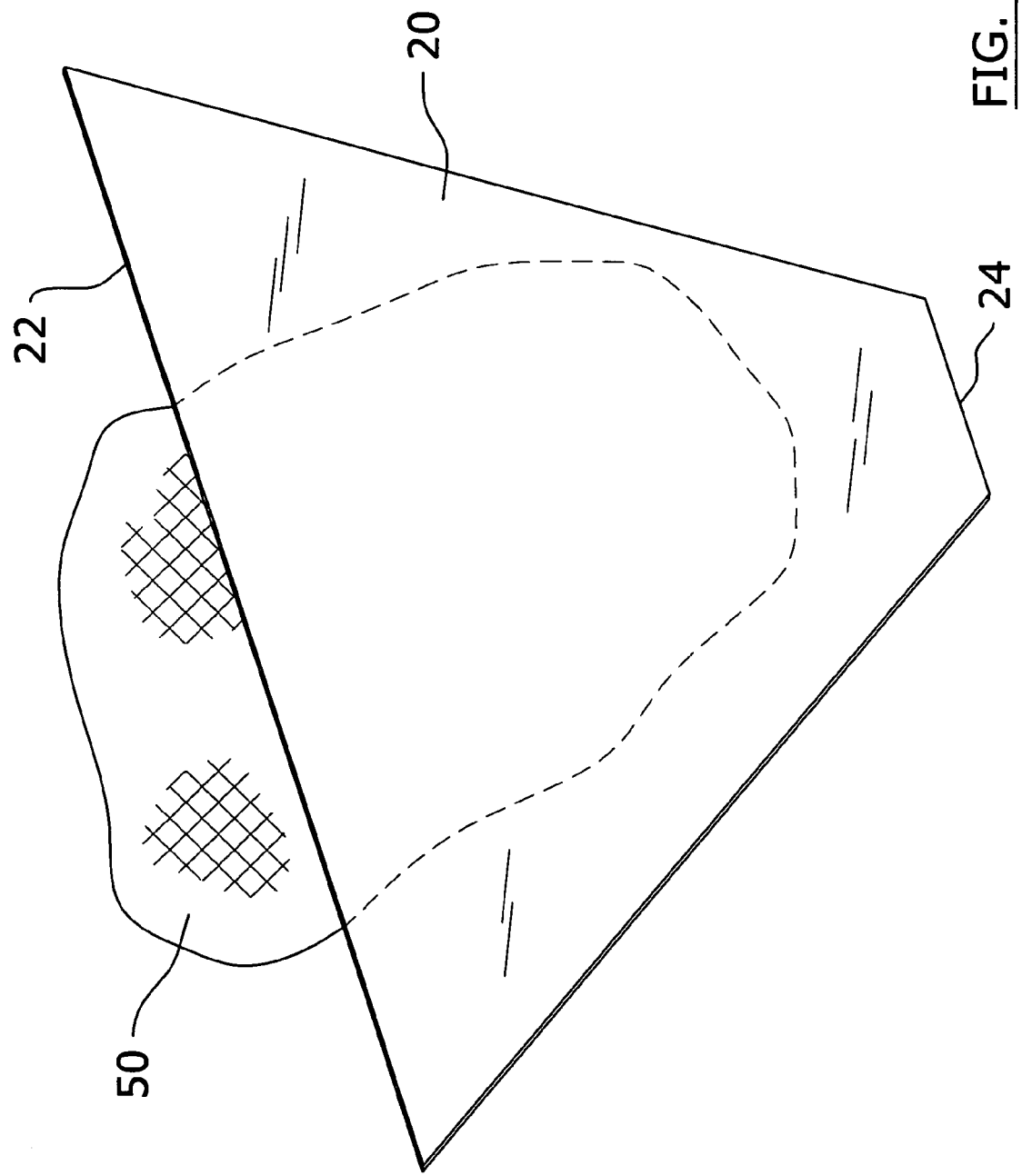
FIG. 4 is a front view of the present invention having the edges removed with the cleansing wipe partially removed within the housing.
Figure 5:
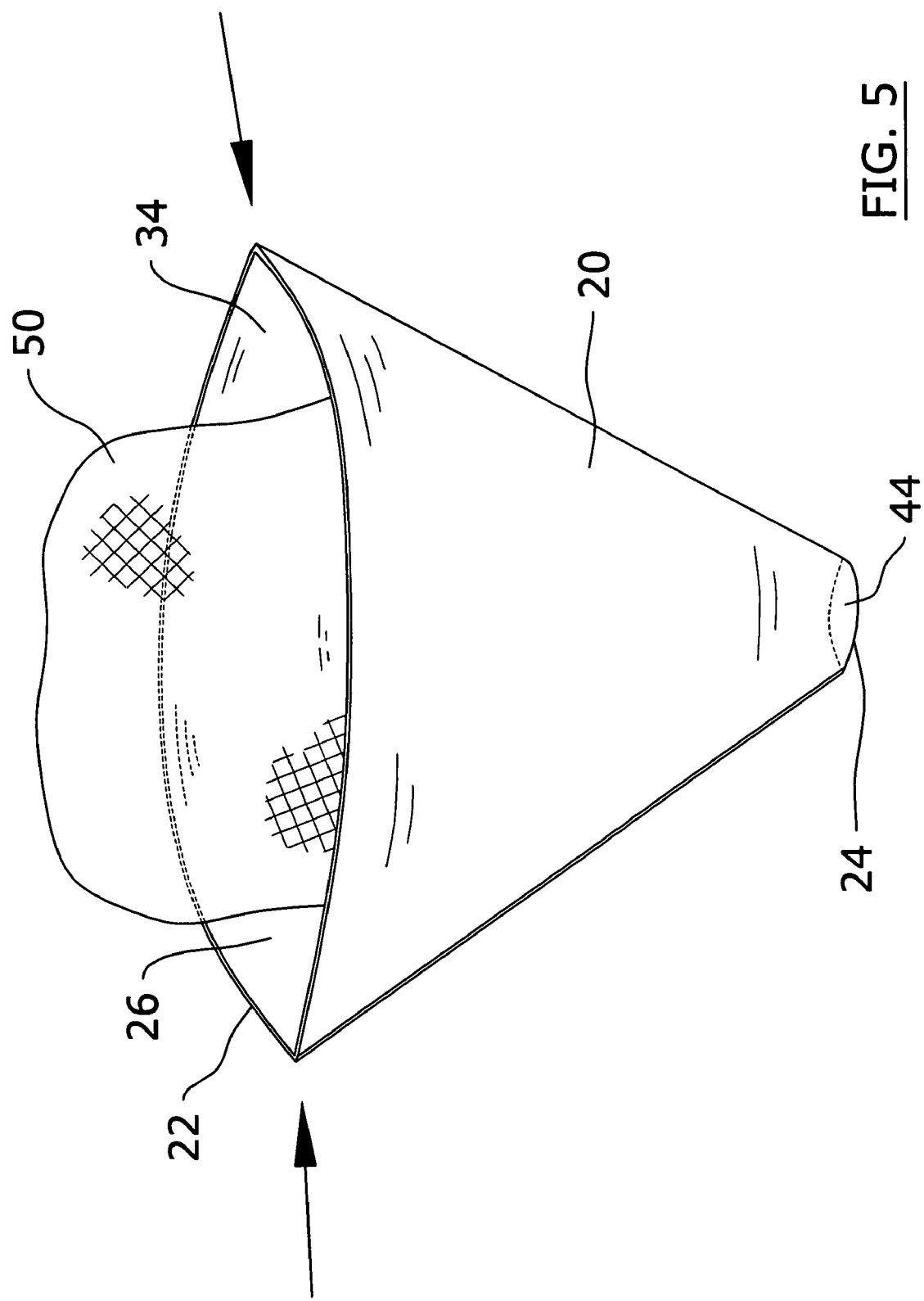
FIG. 5 is an upper perspective view of the present invention wherein the housing has a three-dimensional substantially conical shape due to pressure applied to the sides of the housing.

Turning now descriptively to the drawings, in which similar reference characters denote similar elements throughout the several views, FIGS. 1 through 8 illustrate a tampon disposal system 10, which comprises a tampon disposal device for efficiently and sanitarily disposing of a soiled tampon 12. The tampon disposal system 10 includes a housing 20 having at least one wall, an inner cavity 26, a first edge 30, a second edge 40 and a cleansing wipe 50 that is enclosed within the housing 20. Removal of the first edge 30 from the housing 20 along a first perforation 32 creates a first opening 34. Removal of second edge 40 from the housing 20 along a second perforation 42 creates a second opening 44. Removal of the first edge 30 and second edge 40 exposes the inner cavity 26 of the housing 20 and the cleansing wipe 50 positioned therein as shown in FIG. 5. Upon removal of the cleansing wipe 50, the tampon string 14 attached to a soiled tampon 12 is insertable through the first opening 34 and exits through the second opening 44 of the housing 20 whereby removal and disposal of the tampon 12 is achieved in a relatively sanitary and efficient manner as illustrated in FIGS. 1, 7 and 8.

B. Housing

Figure 2:
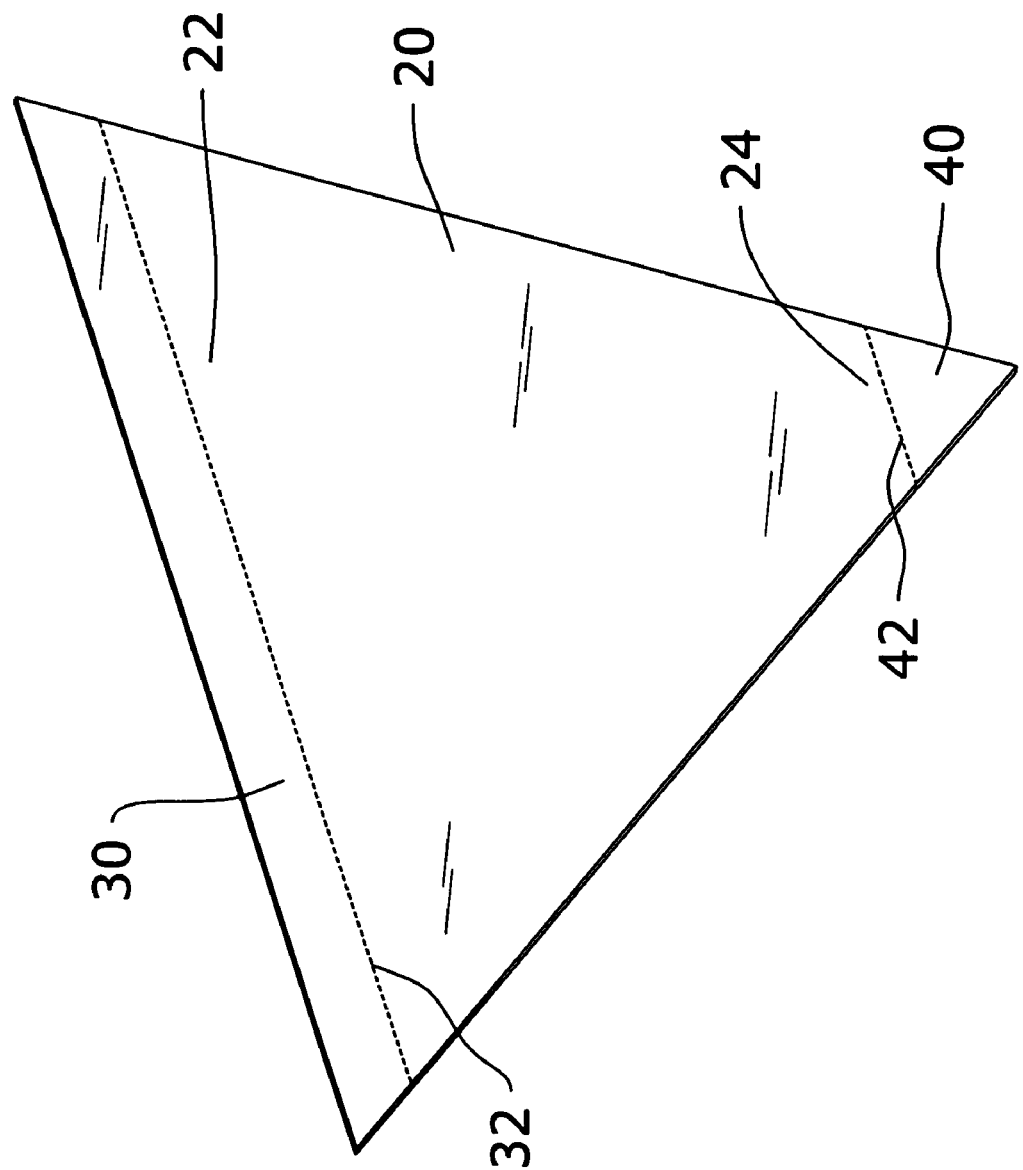
FIG. 2 is an upper perspective view of the present invention as packaged with the edges still attached.

As shown in FIG. 2, the housing 20 as packaged preferably consists of a flat triangle shaped structure. The housing 20 also has an inner cavity 26 as shown in FIGS. 1, 5 and 6. The housing 20 is preferably made of cardboard or other non-absorbent material. The housing 20 has a first perforation 32 positioned between the housing 20 and the first edge 30, and a second perforation 42 positioned between the housing 20 and the second edge 40. The first edge 30 preferably extends across a first end 22 of the housing 20, and the second edge 40 preferably extends across a second end 24 of the housing 20 opposite the first end 22 as shown in FIGS. 2 and 3.

Upon removal of the first edge 30 and the second edge 40, a first opening 34 is created where the first perforation 32 was positioned and a second opening 44 is created where the second perforation 42 was positioned as shown in FIG. 5. The first opening 34 is preferably positioned on the first end 22 and the second opening 44 is preferably positioned on the second end 24 of the housing 20. A cleansing wipe 50 is exposed from the first opening 34 at the first end 22 of the housing 20 as shown in FIGS. 4 and 5. The housing 20 preferably has a flat trapezoidal shape after removal of the first edge 30 and second edge 40 as shown in FIG. 4. Application of pressure on the sides nearest the first end 22 of the housing 20 causes the housing 20 to substantially form a funnel shape as shown in FIGS. 1, 5 and 6.

C. Edges

There are preferably two edges 30, 40 as shown in FIGS. 2 and 3. The housing 20 preferably has a first perforation 32 between the housing 20 and the first edge 30, and a second perforation 42 between the housing 20 and the second edge 40 that facilitate manual detachment of the first edge 30 and the second edge 40 from the housing 20. Removal of the first edge 30 and second edge 40 of the housing 20 exposes the inner cavity 26 of the housing 20, and creates the first opening 32 and second opening 34 where the first edge 30 and second edge 40 were previously positioned as shown in FIGS. 1, 5 and 6.

D. Cleansing Wipe

The cleansing wipe 50 is found within the housing 20 as shown in FIGS. 4 and 5. The cleansing wipe 50 is preferably made of a material that will not clog a toilet upon flushing the toilet. Upon removal of the first edge 30 and second edge 40, the cleansing wipe 50 is exposed and may be removed from the inner cavity 26 of the housing 20 as shown in FIGS. 4 and 5. The cleansing wipe 50 may then be used for any purpose the user sees fit.

E. In Use

In use, when a user desires to remove a soiled tampon 12, the user tears the edges 30, 40 off of the housing 20 along the perforations 32, 42, thereby removing the first edge 30 and second edge 40 from the housing 20 as shown in FIG. 3. The user then removes the cleansing wipe 50 from inner cavity 26 of the housing 20.

Upon removal of the cleansing wipe 50, the user then applies pressure to the sides of the housing 20 nearest the first end 22 of the housing 20 to expand the housing 20 as shown in FIG. 5. Applying pressure to the sides of the housing 20 gives the housing 20 a funnel shape with a first opening 34 on the first end 22 and a second opening 44 on the second end 24 as illustrated in FIGS. 1, 5 and 6. The user inserts the tampon string 14 of a soiled tampon 12 into the first opening 34 at the first end 22 of the housing 20 and the string 14 passes out the second opening 34 at the second end 24 of the housing 20 as shown in FIGS. 1 and 7. The user then pulls the tampon string 14 of the tampon 12 if the tampon 12 is not accessible, or the user can also wrap the housing 20 directly around the exposed portion of the tampon 12 to efficiently remove the tampon 12 as shown in FIG. 8.

Upon removal of the soiled tampon 12, the housing 20 and soiled tampon 12 may be discarded. The cardboard composition of the housing 20 prevents any fluids from contacting the hands of the user during the removal process. The cardboard composition also encourages the user to throw the used tampon 12 and tampon removal system 10 into the refuse container 16 as opposed to the toilet as shown in FIG. 8.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

I claim:

1. A method of utilizing a tampon disposal system comprising a housing having a first end and a second end, wherein said housing includes a first edge within said first end and a first perforation for allowing selective removal of said first edge to expose a first opening within said first end, and wherein said housing includes a second edge within said second end and a second perforation for allowing selective removal of said second edge to expose a second opening within said second end, said method comprising the steps of:
- removing said first edge from said housing;
- removing said second edge from said housing;
- expanding said housing into a hollow shape;
- passing a tampon string through said first opening and then through said second opening;
- pulling upon said tampon string thereby drawing a tampon into an inner cavity of said housing; and
- disposing of said housing with said tampon positioned within.

2. The method of utilizing a tampon disposal system of claim 1, including removing a cleansing wipe from within said housing prior to said passing a tampon string.

3. The method of utilizing a tampon disposal system of claim 1, wherein said first end is broader than said second end.

4. The method of utilizing a tampon disposal system of claim 1, wherein said housing tapers from said first end to said second end.

5. The method of utilizing a tampon disposal system of claim 1, wherein said housing is comprised of a disposable and flexible material.

6. The method of utilizing a tampon disposal system of claim 1, wherein said second opening is large enough to freely receive a tampon string and small enough to prevent passage of a tampon.

7. The method of utilizing a tampon disposal system of claim 1, wherein said first perforation and said second perforation are substantially parallel to one another.

8. The method of utilizing a tampon disposal system of claim 1, wherein said housing forms a conical structure when said first edge and said second edge are removed.

9. The method of utilizing a tampon disposal system of claim 1, wherein said housing has a substantially triangular shape.

10. The method of utilizing a tampon disposal system of claim 9, wherein said housing is substantially flat until after said first edge and said second edge are removed.

* * * * *